US012596127B2

(12) United States Patent
Delcourt et al.

(10) Patent No.: US 12,596,127 B2
(45) Date of Patent: Apr. 7, 2026

(54) PREDICTION OF THE CONTENT OF OMEGA-3 POLYUNSATURATED FATTY ACIDS IN THE RETINA BY MEASURING 7 CHOLESTEROL ESTER MOLECULES

(71) Applicants: UNIVERSITE DE BORDEAUX, Berland (FR); INSERM (INSTITUT NATIONAL DE LA SANTÉ ET DE LA RECHERCHE MÉDICALE), Paris (FR); INSTITUT NATIONAL DE RECHERCHE POUR L'AGRICULTURE, L'ALIMENTATION ET L'ENVIRONNEMENT, Paris (FR); UNIVERSITE DE BOURGOGNE, Dijon (FR); INSTITUT NATIONAL SUPERIEUR DES SCIENCES AGRONOMIQUES DE L'ALIMENTATION ET DE L'ENVIRONNEMENT, Dijon (FR)

(72) Inventors: Cécile Delcourt, Bordeaux (FR); Niyazi Acar, Longchamp (FR); Lionel Bretillon, Dijon (FR); Soufiane Ajana, Bourdeaux (FR); Hélène Jacqmin-Gadda, Gradignan (FR); Boris Hejblum, Talence (FR); Bénédicte Merle, Bordeaux (FR)

(73) Assignees: UNIVERSITE DE BORDEAUX, Berland (FR); INSERM (INSTITUT NATIONAL DE LA SANTE ET DE LA RECHERCHE MEDICALE, Paris (FR); INSTITUT NATIONAL DE RECHERCHE POUR L'AGRICULTURE, L'ALIMENTATION ET L'ENVIRONNEMENT, Paris (FR); UNIVERSITE DE BOURGOGNE, Dijon (FR); INSTITUT NATIONAL SUPERIEUR DES SCIENCES AGRONOMIQUES DE L'ALIMENTATION ET DE L'EVIRONNEMENT, Dijon (FR)

( * ) Notice: Subject to any disclaimer, the term of this patent is extended or adjusted under 35 U.S.C. 154(b) by 1024 days.

(21) Appl. No.: 17/762,928

(22) PCT Filed: Sep. 24, 2020

(86) PCT No.: PCT/FR2020/051666
§ 371 (c)(1),
(2) Date: Mar. 23, 2022

(87) PCT Pub. No.: WO2021/058914
PCT Pub. Date: Apr. 1, 2021

(65) Prior Publication Data
US 2022/0373567 A1     Nov. 24, 2022

(30) Foreign Application Priority Data

Sep. 24, 2019   (FR) ...................................... 19 10515

(51) Int. Cl.
*G01N 33/92*       (2006.01)

(52) U.S. Cl.
CPC ....... *G01N 33/92* (2013.01); *G01N 2800/164* (2013.01); *G01N 2800/52* (2013.01)

(58) Field of Classification Search
CPC ............ G01N 33/92; G01N 2800/164; G01N 2800/52
See application file for complete search history.

(56) References Cited

FOREIGN PATENT DOCUMENTS

EP          2619586 B1 * 10/2014 ............. G01N 33/92

OTHER PUBLICATIONS

Bretillon et al. ("Would Circulating Cholesteryl Esters be Considered as Markers to Fatty Acid composition of the Human Retina?," ARVO Annual Meeting Abstract, Apr. 2010). (Year: 2010).*
Acar et al: "Identification of a circulating biomarker highly associated to retinal omega-3 polyunsaturated fatty acid content: the Blisar project", Invest. Ophth. Vis.Sci., vol. 60, p. 1-2, Jul. 2019.
Bretillon et al: "Validation of the use of a circulating biomarker of retinal omega-3 polyunsaturated fatty acids in supplementation conditions: the BLISAR project", Invest. Ophth. Vis.Sci., vol. 60, p. 1-2, Jul. 2019.
Merle et al: "High concentrations of plasma n3 fatty acids are associated with decreased risk for late age-related macular degeneration", J. Nutr., vol. 143, No. 4, p. 505-511, Apr. 2013.
Merle et al: "Circulating omega-3 fatty acids and neovascular age-related macular degeneration", Invest. Opthalmol. Sci., vol. 55, No. 3, p. 2010-2019, Mar. 28, 2014.
Prokopiou et al: "Therapeutic potential of omega-3 fatty acids supplementation in a mouse model of dry macular degeneration", BMJ Open Opth., vol. 1, p. 1-12, 2017.

* cited by examiner

*Primary Examiner* — Jill A Warden
*Assistant Examiner* — Michael Stanley Gzybowski
(74) *Attorney, Agent, or Firm* — WCF IP

(57) ABSTRACT

The present invention relates to a method for determining the content of omega-3 polyunsaturated fatty acids in the retina of a subject comprising the determination of the content of at least one cholesteryl ester in a blood sample from said subject, the content of omega-3 polyunsaturated fatty acids in the retina being correlated to the content of said at least one cholesteryl ester, said at least one cholesteryl ester being cholesteryl 5,8,11,14,17-eicosapentaenoate.

5 Claims, No Drawings

PREDICTION OF THE CONTENT OF OMEGA-3 POLYUNSATURATED FATTY ACIDS IN THE RETINA BY MEASURING 7 CHOLESTEROL ESTER MOLECULES

TECHNICAL FIELD

The invention relates to the field of ophthalmology and more specifically to the prediction of the content of omega-3 polyunsaturated fatty acids in the retina.

PRIOR ART

Age-related macular degeneration (AMD) is a degenerative disease of the central part of the retina, known as the macula. It affects mainly elderly people and is responsible for 50% of the cases of blindness in industrialized countries. Around 600 000 people are affected by the disease in France. The advanced forms of AMD (known as neovascular AMD and atrophic AMD) are associated with a loss of vision, and are generally preceded by early and asymptomatic anomalies.

The etiology of AMD is multifactorial, and involves genetic factors and also environmental factors such as food. In this context, the role of omega-3 polyunsaturated fatty acids or omega-3 is arousing increasing interest for 3 reasons:

omega-3 polyunsaturated fatty acids, and in particular docosahexaenoic acid (DHA), are major constituents of the retina where they prevent certain pathological processes observed in AMD such as inflammation, neovascularization and cell death;

studies have shown a depletion of the content of omega-3 polyunsaturated fatty acids in the retina of subjects suffering from AMD;

more than 20 epidemiological studies have shown, very consistently, a 40% reduction in the risk of AMD in subjects having a dietary intake high in omega-3 polyunsaturated fatty acids.

This data therefore suggests a protective effect of omega-3 polyunsaturated fatty acids against AMD.

The family of omega-3 polyunsaturated fatty acids encompasses in particular a precursor fatty acid, α-linoleic acid (or C18:3n-3 or ALA) and three long-chain derivatives, eicosapentaenoic acid (or C20:5n-3 or EPA), docosapentaenoic acid (or C22:5n-3 or DPAn-3) and docosahexaenoic acid (DHA or C22:6n-3). ALA is an essential nutrient for humans, since animal organisms are incapable of synthesizing it de novo, and therefore depend exclusively on a dietary intake. The synthesis of EPA, DPAn-3 and DHA from ALA is possible in humans but is very limited. It is therefore recommended to also provide these fatty acids through a diet rich in fish and seafood. Despite these recommendations, the dietary intakes of omega-3 polyunsaturated fatty acids of the French remain below the recommendations issued by health agencies.

It is therefore essential to be able to determine the content of omega-3 polyunsaturated fatty acids in the retina.

Knowing the concentrations of omega-3 polyunsaturated fatty acids in the retina is in fact important information for: 1. identifying subjects whose retina is depleted and who could therefore be at risk of AMD, and 2. monitoring the effectiveness of a nutritional supplement based on omega-3 polyunsaturated fatty acids in restoring the physiological contents of these fatty acids in the retina.

For obvious ethical reasons, it is however impossible to carry out biopsies of the retina in humans in vivo for the purpose of a biochemical assay of its content of omega-3 polyunsaturated fatty acids. Consequently, an indirect measurement is required.

The measurement in the blood or plasma of the omega-3 polyunsaturated fatty acids is also not sufficient to determine the content of omega-3 polyunsaturated fatty acids in the retina.

It is therefore necessary to obtain a robust and reliable method for determining the content of omega-3 polyunsaturated fatty acids in the retina.

Three studies have attempted to correlate the content of circulating fatty acid with that of the retina. The first study limited itself to studying the associations of the retinal contents of omega-3 polyunsaturated fatty acids with the blood contents of various fatty acids, without attempting to predict the content of omega-3 polyunsaturated fatty acids in the retina, or investigating the lipid structures which carry the fatty acids in the blood (phospholipids, cholesteryl esters, triglycerides, etc.) (Gorusupudi et al., J. Lipid Res., 2016; 57: 499-508). The second identified cholesteryl esters as a whole as circulating markers of the DHA content of the retina (Bretillon et al., Exp. Eye Res., 2008; 87: 521-528). The third showed that the DHA content of erythrocytes was not a good circulating marker of the DHA content of the retina (Acar et al., PLoS ONE 2012; 7: e35102).

None of these studies considered the overall content of omega-3 polyunsaturated fatty acids in the retina (they targeted DHA or else ratios of concentrations of omega-6 fatty acids/omega-3 fatty acids).

Nor did they make it possible to construct a model for estimating the true content of omega-3 polyunsaturated fatty acids such that it could be measured through a direct analysis.

To date, two approaches are commonly used to indirectly evaluate the retinal content of omega-3 polyunsaturated fatty acids. The first is based on dietary intakes which, through dietary questionnaires, make it possible to evaluate, in a subject, the consumption of such and such food rich in omega-3 polyunsaturated fatty acids and to extrapolate it to a tissue enrichment. The second consists of an evaluation of the contents of circulating omega-3 polyunsaturated fatty acids and here too of extrapolating a blood enrichment to a tissue enrichment. This evaluation in the blood compartment may be more or less global and concern both the total blood, erythrocytes, the total plasma or else various compartments of the plasma (phospholipids and cholesteryl esters mainly).

The use of dietary intakes is confronted with a large number of difficulties, and in particular those linked to dietary evaluation methods: length and complexity of the dietary questionnaires, memory bias, difficulties in taking into account the great complexity and the daily variability of the human diet, inaccuracies in estimating the amounts of food ingested and in the nutrient content of the foods, etc.

Regarding the use of the lipid composition of the plasma/ of the various compartments of the plasma, this is based on the supposition that the fatty acid composition of the peripheral tissues (including the retina) follows the same pattern as that of the plasma. However, it is known that the relationship between dietary lipids, plasma lipids and tissue lipids is non-linear as it is regulated by several other factors such as metabolism, genetics, age, sex or lifestyle (smoking, alcohol consumption, physical activity). To date, no study has shown the absolute validity or otherwise of such and such compartment in the estimation of the content of fatty acids in the retina, apart from the two preliminary studies previously mentioned that show the invalidity of the use of erythrocytes in an adult human subject and on the contrary the advantage of cholesteryl esters in their entirety.

Technical Problem

Thus, and despite major medical interest, it is impossible to date to measure the content of omega-3 polyunsaturated fatty acids in the retina in a reliable manner. It is therefore necessary to provide a tool for evaluating the omega-3 polyunsaturated fatty acids in the retina, other than the dietary intake method which is complex to carry out and imprecise and other than the method based on the lipid composition of plasma/various plasma compartments which does not make it possible to obtain reliable results regarding the content of fatty acids in the retina.

Advantageously, the invention makes it possible to estimate the content of omega-3 polyunsaturated fatty acids in the retina by way of the blood assay of at least one cholesteryl ester.

The inventors have, by refinement in the use of cholesteryl esters as a marker of the content of omega-3 polyunsaturated fatty acids in the retina, used values of an assay of one cholesteryl ester, preferentially of seven cholesteryl esters, instead of the 25 present in the blood.

The method, based on the determination of the content of cholesteryl esters, enables a better robustness of the prediction, and this is in comparison with the studies and approaches that have determined the contents of omega-3 polyunsaturated fatty acids in red blood cells and whole blood (r=0.62 versus r=0.40 for the omega-3 fatty acids of the total lipids of plasma and r=0.14 for the omega-3 fatty acids of red blood cells).

Specifically, the construction and use of a mathematical model advantageously makes it possible to predict the concentration of omega-3 polyunsaturated fatty acids in the retina from a value of an assay of one cholesteryl ester, preferentially of 7 cholesteryl esters in the blood.

This approach is advantageously based on a small number of plasma cholesteryl esters, and is more effective and reliable for determining the retinal content of omega-3 polyunsaturated fatty acids.

Thus, one subject of the present invention is a method for determining the content of omega-3 polyunsaturated fatty acids in the retina of a subject comprising the quantification of the content of at least one cholesteryl ester in a blood sample from said subject, the content of omega-3 polyunsaturated fatty acids in the retina being correlated to the content of cholesteryl esters.

Another subject of the invention is a method for preventing a retinal pathology linked to a deficit of omega-3 polyunsaturated fatty acids by the determination of the content of omega-3 polyunsaturated fatty acids in the retina according to the determination method according to the invention.

The invention also relates to a method for monitoring the treatment of a pathology linked to a deficit of omega-3 polyunsaturated fatty acids comprising the steps of administering at least one treatment and of determining the content of omega-3 polyunsaturated fatty acids in the retina according to the determination method of the invention.

The invention also relates to a method for diagnosis of deficiencies in omega-3 polyunsaturated fatty acids comprising the determination of the content of omega-3 polyunsaturated fatty acids in the retina of a patient to whom the treatment has been administered, according to the determination method of the invention.

SUMMARY OF THE INVENTION

Method for Determining the Content of Omega-3 Polyunsaturated Fatty Acids

The present invention relates to a method for determining the content of omega-3 polyunsaturated fatty acids in the retina of a subject comprising the determination of the content of at least one cholesteryl ester in a blood sample from said subject, the content of omega-3 polyunsaturated fatty acids in the retina being correlated to the content of said at least one cholesteryl ester, said at least one cholesteryl ester being cholesteryl 5,8,11,14,17-eicosapentaenoate.

Specifically, and advantageously, the inventors of the present invention have demonstrated that the determination of the content of cholesteryl 5,8,11,14,17-eicosapentaenoate (C20:5 ω3 methyl ester), preferentially contained in the plasma, makes it possible to predict the content of omega-3 polyunsaturated fatty acids in the retina of a subject.

The expression "content of omega-3 polyunsaturated fatty acids in the retina" is understood to mean the sum, as a weight percentage of the total fatty acids, of all of the omega-3 polyunsaturated fatty acids present in the retina, namely the sum, as a weight percentage of the total fatty acids, of α-linoleic acid (or C18:3n-3 or ALA), of eicosapentaenoic acid (or C20:5 ω-3 or EPA), of docosapentaenoic acid (or C22:5 ω-3 or DPA ω-3) and of docosahexaenoic acid (DHA or C22:6 ω-3).

According to one embodiment of the determination method, the content of at least six additional cholesteryl esters is determined.

The cholesteryl esters are chosen from cholesteryl tetradecanoate, cholesteryl pentadecanoate, cholesteryl hexadecanoate, cholesteryl 7-hexadecenoate, cholesteryl 9-hexadecenoate, cholesteryl heptadecanoate, cholesteryl octadecanoate, cholesteryl trans-9-octadecenoate, cholesteryl cis-9-octadecenoate, cholesteryl 11-octadecenoate, cholesteryl 9,12-octadecadienoate, cholesteryl eicosanoate, cholesteryl 6,9,12-octadecatrienoate, cholesteryl 11-eicosenoate, cholesteryl 9,12,15-octadecatrienoate, cholesteryl 11,14-eicosadienoate, cholesteryl 5,8,11-eicosatrienoate, cholesteryl 8,11,14-eicosatrienoate, cholesteryl 5,8,11,14-eicosatetraenoate, cholesteryl 15-tetracosenoate, cholesteryl 7,10,13,16-docosatetraenoate, cholesteryl 4,7,10,13,16-docosapentaenoate, cholesteryl 7,10,13,16,19-docosapentaenoate, and cholesteryl 4,7,10,13,16,19-docosahexaenoate.

The nomenclature of the cholesteryl esters is given in detail in table 1.

TABLE 1

| | Biologist's nomenclature | Chemist's nomenclature |
|---|---|---|
| 1 | C14:0 cholesteryl ester | cholesteryl tetradecanoate |
| 2 | C15:0 cholesteryl ester | cholesteryl pentadecanoate |
| 3 | C16:0 cholesteryl ester | cholesteryl hexadecanoate |
| 4 | C16:1 ω-9 cholesteryl ester | cholesteryl 7-hexadecenoate |
| 5 | C16:1 ω-7 cholesteryl ester | cholesteryl 9-hexadecenoate |
| 6 | C17:0 cholesteryl ester | cholesteryl heptadecanoate |

TABLE 1-continued

| Biologist's nomenclature | Chemist's nomenclature |
|---|---|
| 7  C18:0 cholesteryl ester | cholesteryl octadecanoate |
| 8  C18:1 ω-9 trans cholesteryl ester | cholesteryl trans-9-octadecenoate |
| 9  C18:1 ω-9 cholesteryl ester | cholesteryl cis-9-octadecenoate |
| 10  C18:1 ω-7 cholesteryl ester | cholesteryl 11-octadecenoate |
| 11  C18:2 ω-6 cholesteryl ester | cholesteryl 9,12-octadecadienoate |
| 12  C20:0 cholesteryl ester | cholesteryl eicosanoate |
| 13  C18:3 ω-6 cholesteryl ester | cholesteryl 6,9,12-octadecatrienoate |
| 14  C20:1 ω-9 cholesteryl ester | cholesteryl 11-eicosenoate |
| 15  C18:3 ω-3 cholesteryl ester | cholesteryl 9,12,15-octadecatrienoate |
| 16  C20:2 ω-6 cholesteryl ester | cholesteryl 11,14-eicosadienoate |
| 17  C20:3 ω-9 cholesteryl ester | cholesteryl 5,8,11 eicosatrienoate |
| 18  C20:3 ω-6 cholesteryl ester | cholesteryl 8,11,14-eicosatrienoate |
| 19  C20:4 ω-6 cholesteryl ester | cholesteryl 5,8,11,14-eicosatetraenoate |
| 20  C20:5 ω-3 cholesteryl ester | cholesteryl 5,8,11,14,17-eicosapentaenoate |
| 21  C24:1 ω-9 cholesteryl ester | cholesteryl 15-tetracosenoate |
| 22  C22:4 ω-6 cholesteryl ester | cholesteryl 7,10,13,16-docosatetraenoate |
| 23  C22:5 ω-6 cholesteryl ester | cholesteryl 4,7,10,13,16-docosapentaenoate |
| 24  C22:5 ω-3 cholesteryl ester | cholesteryl 7,10,13,16,19-docosapentaenoate |
| 25  C22:6 ω-3 cholesteryl ester | cholesteryl 4,7,10,13,16,19-docosahexaenoate |

According to one embodiment, the 6 additional cholesteryl esters are cholesteryl 9,12,15-octadecatrienoate, cholesteryl 4,7,10,13,16,19-docosahexaenoate, cholesteryl 9,12-octadecadienoate, cholesteryl 6,9,12-octadecatrienoate, cholesteryl 8,11,14-eicosatrienoate, cholesteryl 5,8,11, 14-eicosatetraenoate.

Thus, and according to one embodiment, the content of 7 cholesteryl esters is determined.

The inventors have in fact identified, besides cholesteryl 5,8,11,14,17-eicosapentaenoate, six additional cholesteryl esters which are cholesteryl 9,12,15-octadecatrienoate, cholesteryl 4,7,10,13,16,19-docosahexaenoate, cholesteryl 9,12-octadecadienoate, cholesteryl 6,9,12-octadecatrienoate, cholesteryl 8,11,14-eicosatrienoate, cholesteryl 5,8,11, 14-eicosatetraenoate, from among the twenty-five present in the blood, which make it possible to obtain a reliable and precise determination of the content of omega-3 polyunsaturated fatty acids in the retina.

The expression "content of at least one cholesteryl ester" is understood to mean the weight percentage of at least one fatty acid of the cholesteryl esters.

A person skilled in the art will be able to use any known method for determining the content of cholesteryl ester.

According to one embodiment and in order to determine the content of cholesteryl ester, one method consists of a step of transesterification.

The transesterification step corresponds to an acid catalysis in which the sterol portion of the cholesteryl ester is exchanged with an alkyl group. The alkyl group is chosen from methyl, propyl or butyl.

According to one embodiment, the transesterification step is a step of transmethylation of the fatty acids of the cholesteryl esters.

The content of cholesteryl ester may in fact be determined by the formation of the methyl esters of the fatty acids of the cholesteryl esters. The methyl esters of the cholesteryl esters are obtained after transmethylation of the fatty acids of the corresponding cholesteryl ester.

Typically, the methyl esters of the fatty acids of the cholesteryl esters are formed after transmethylation of the fatty acids according to the method of Morrison & Smith (Morrison & Smith, J. Lipid Res., 1964; 53: 600-608).

The methyl esters of the fatty acids of the cholesteryl esters identified according to the present invention are 9,12,15-octadecatrienoic acid methyl ester (C18:3 ω-3 methyl ester), 4,7,10,13,16,19-docosahexaenoic acid methyl ester (C22:6 ω-3 methyl ester), 9,12-octadecadienoic acid methyl ester (C18:2 ω-6 methyl ester), 6,9,12-octadecatrienoic acid methyl ester (C18:3 ω-6 methyl ester), 8,11,14-eicosatrienoic acid methyl ester (C20:3 ω-6 methyl ester), 5,8,11,14-eicosatetraenoic acid methyl ester (020:4 ω-6 methyl ester), 5,8,11,14,17-eicosapentaenoate acid methyl ester (C20:5 ω-3 methyl ester).

According to one embodiment, the relative weight content of each of the 25 methyl esters of fatty acids of the cholesteryl esters is determined.

The relative weight content of the methyl esters of the fatty acids is analysed and determined by any method known to a person skilled in the art, typically by gas chromatography coupled to flame ionization detection, as described in Acar et al. (Acar et al. PLoS One 2012; 7(4): e35102).

The relative proportions of the 25 species of methyl esters are calculated and expressed as a percentage of the total fatty acids of the cholesteryl esters. Typically, the proportions are calculated, from any data integration software known to a person skilled in the art, for example using the EZChrom Elite software (Agilent Technologies, Massy, France) and are expressed as a percentage of the total fatty acids of the cholesteryl esters.

This step makes it possible to determine the weight percentage of at least one fatty acid of the cholesteryl esters and therefore determine the content of each cholesteryl ester.

The term "correlation" is understood to mean the calculation of the estimated value of the content of omega-3 polyunsaturated fatty acids in the retina from the content of at least one cholesteryl ester, preferentially from the content of at least 7 cholesteryl esters and more preferentially from the content of 7 cholesteryl esters.

Typically, the content of omega-3 polyunsaturated fatty acids in the retina is estimated using an algorithm based on the content of at least 1 cholesteryl ester, preferentially based on the content of at least 7 cholesteryl esters and more preferentially using an algorithm based on the content of 7 cholesteryl esters.

Typically, the calculation is carried out by any algorithm which makes it possible to predict, for a new sample, the content of omega-3 polyunsaturated fatty acids in the retina from the assay of at least 1 cholesteryl ester, preferentially from at least 7 cholesteryl esters and more preferentially from 7 cholesteryl esters.

By way of illustration and for the determination of the content of omega-3 polyunsaturated fatty acids in the retina from a cholesteryl ester, the algorithm is based on a linear regression according to the formula:

$$(4.1717 \times C20:5\ \omega 3\ EC) \qquad \text{[Math. 1]}$$

where C20:5 ω3 EC corresponds to the content of cholesteryl 5,8,11,14,17-eicosapentaenoate, centered and reduced according to the distribution in the training sample (see table 2 below).

Also by way of illustration, and for the determination of the content of omega-3 polyunsaturated fatty acids in the retina from at least 7 cholesteryl esters, the algorithm is based on the sparse group partial least squares (sgPLS) method described by Liquet et al. (Liquet B et al., Bioinformatics, 2016 Jan. 1; 32(1): 35-42).

The algorithm comprises and preferably consists of 4 steps:

1. Several sums and ratios are calculated from the assay of at least seven cholesteryl esters. The assay of cholesteryl esters contained in the plasma is an indirect assay. The cholesteryl esters undergo a transesterification which results in fatty acid methyl esters. The fatty acid methyl esters thus obtained are quantified by known methods, for example by gas chromatography. The relative amount of a fatty acid methyl ester corresponds to a percentage of the total fatty acid methyl esters.

In one embodiment, the sums and ratios present in the mathematical formula reproduced below (math. 2), are calculated from assays of the 7 molecules of interest resulting from the 25 cholesteryl ester fatty acid methyl esters.

The 7 molecules of interest resulting from the 25 cholesteryl ester fatty acid methyl esters are the following: 9,12,15-octadecatrienoic acid methyl ester (C18:3 ω-3 methyl ester), 5,8,11,14,17-eicosapentaenoic acid methyl ester (C20:5 ω-3 methyl ester), 4,7,10,13,16,19-docosahexaenoic acid methyl ester (C22:6 ω-3 methyl ester), 9,12-octadecatrienoic acid methyl ester (C18:2 ω-6 methyl ester), 6,9,12-octadecatrienoic acid methyl ester (C18:3 ω-6 methyl ester), 8,11,14-eicosatrienoic acid methyl ester (020:3 ω-6 methyl ester), 5,8,11,14-eicosatrienoic acid methyl ester (C20:4 ω-6 methyl ester).

The mathematical formula is given in detail below $$\begin{aligned} &(0.117939545 \times C20:5\omega3\_EC) + (0.000429538 \times C22:\\ &6\omega3\_EC) + (0.127303513 \times Tot\_\omega3\_EC) -\\ &(0.089285375 \times ratio\_\omega6\_\omega3\_EC) + (0.12438627 \times\\ &ratio\_diet\omega3\_\omega6\_EC) + (0.095117859 \times\\ &ratio\_EPADPA\omega3DHA\_AA\_EC) -\\ &(0.086291782 \times ratio\_AA\_EPA\_EC) +\\ &(0.115467043 \times tot\_\omega3\_LC\_EC) \qquad \text{[Math. 2]:} \end{aligned}$$

in which:

C20:5ω3_EC corresponds to the content of cholesteryl 5,8,11,14,17-eicosapentaenoate;

C22:6ω3_EC corresponds to the content of cholesteryl 4,7,10,13,16,19-docosahexaenoate;

Tot_ω3_EC corresponds to the sum of the contents of cholesteryl 9,12,15-octadecatrienoate, cholesteryl 5,8,11,14,17-eicosapentaenoate, cholesteryl 7,10,13,16,19-docosapentaenoate and cholesteryl 4,7,10,13,16,19-docosahexaenoate;

ratio_ω6_ω3 EC corresponds to the ratio of the sum of the contents of cholesteryl 9,12-octadecadienoate, cholesteryl 6,9,12-octadecatrienoate, cholesteryl 11,14-eicosadienoate, cholesteryl 5,8,11,14-eicosatetraenoate, cholesteryl 7,10,13,16-docosatetraenoate and cholesteryl 4,7,10,13,16-docosapentaenoate to the sum of the contents of cholesteryl 9,12,15-octadecatrienoate, cholesteryl 5,8,11,14,17-eicosapentaenoate, cholesteryl 7,10,13,16,19-docosapentaenoate and cholesteryl 4,7,10,13,16,19-docosahexaenoate;

ratio_diet ω3_ω6 EC corresponds to the ratio of the sum of the contents of cholesteryl 9,12,15-octadecatrienoate, cholesteryl 5,8,11,14,17-eicosapentaenoate and cholesteryl 4,7,10,13,16,19-docosahexaenoate to the content of cholesteryl 9,12-octadecadienoate;

ratio_EPADPAω3DHA_AA_EC corresponds to the ratio of the sum of the contents of cholesteryl 5,8,11,14,17-eicosapentaenoate, cholesteryl 7,10,13,16,19-docosapentaenoate and cholesteryl 4,7,10,13,16,19-docosahexaenoate to the content of cholesteryl 5,8,11,14-eicosatetraenoate;

ratio_AA_EPA_EC corresponds to the ratio of the content of cholesteryl 5,8,11,14-eicosatetraenoate to the content of cholesteryl 5,8,11,14,17-eicosapentaenoate;

tot_ω3_LC_EC corresponds to the sum of the contents of cholesteryl 5,8,11,14,17-eicosapentaenoate, cholesteryl 7,10,13,16,19-docosapentaenoate and cholesteryl 4,7,10,13,16,19-docosahexaenoate.

2. All of the parameters are centered and reduced using the means and standard deviations of the training sample (the test sample being assumed to result from the same distribution as the training sample).

The means and standard deviations of the training sample are provided in the following table:

TABLE 2

|  | Mean | Standard deviation |
|---|---|---|
| C20:5ω3_EC | 0.70065217 | 0.43111948 |
| C22:6ω3_EC | 0.56717391 | 0.21281879 |
| Tot_ω3_EC | 1.75413043 | 0.61243984 |
| ratio_ω6_ω3_EC | 31.3562904 | 12.3336094 |
| ratio_dietω3_ω6_EC | 0.04338134 | 0.01719207 |
| ratio_EPADPAω3DHA_AA_EC | 0.20686941 | 0.11487994 |
| ratio_AA_EPA_EC | 11.3806181 | 4.69275976 |
| tot_ω3_LC_EC | 1.26782609 | 0.55703945 |

3. Calculation of the mathematical formula from the centered-reduced test sample.

4. In order to obtain the prediction of the concentration of omega-3 polyunsaturated fatty acids in the retina, the result obtained in step 3 is multiplied by the standard deviation of the concentration of omega-3 polyunsaturated fatty acids in the retina of the training sample. The values thus obtained are added to the mean of the concentration of omega-3 polyunsaturated fatty acids in the retina of the training sample.

The standard deviation and mean of the concentration of omega-3 polyunsaturated fatty acids in the retina of the training sample are the following:

Mean: 16.64348

Standard deviation: 2.915459

The expression "training sample" is understood to mean a sample of 46 post-mortem donors, to which the sgPLS method was applied in order to obtain the prediction algorithm.

The expression "test sample" is understood to mean a blood sample from the subject for whom it is desired to determine the retinal content of omega-3 fatty acids.

According to the method according to the invention, the blood sample is chosen from whole blood, serum and plasma.

Preferentially, the sample is plasma.

In one embodiment, the method according to the invention comprises a step of blood collection and of isolating the plasma. A person skilled in the art will be able to use any known method for isolating the plasma. Typically, the plasma will be able to be separated from the red blood cells by centrifuging a sample of whole blood.

The method according to the invention further comprises a step of extracting the total lipids.

The total lipids will themselves be able to be extracted from a blood sample, by any method known to a person skilled in the art. Typically, the total lipids of the plasma, blood and serum are extracted by the method of Moilanen & Nikkari (Moilanen & Nikkari, Clin. Chim. Acta. 1981; 114(1): 111-116).

The method according to the invention further comprises a step of isolating the cholesteryl esters from the total lipids.

Typically, the cholesteryl esters will be isolated from the total lipids by any method known to a person skilled in the art. By way of illustration, the cholesteryl esters are isolated from the total lipids according to a procedure described in Bretillon et al. 2008 (Bretillon et al., Exp. Eye Res., 2008; 87(6): 521-528).

Method for Preventing a Retinal Pathology Linked to a Deficit of Omega-3 Polyunsaturated Fatty Acids The invention relates to a method for preventing a retinal pathology linked to a deficit of omega-3 polyunsaturated fatty acids comprising the determination of the content of omega-3 polyunsaturated fatty acids in the retina according to the method for determining the content of omega-3 polyunsaturated fatty acids according to the invention.

The expression "retinal pathology linked to a deficit of omega-3 polyunsaturated fatty acids" is understood to mean any pathology associated, at least in part, with a reduction in the content of polyunsaturated fatty acids in the retina.

Specifically, as major components of the human retina, omega-3 polyunsaturated fatty acids, and in particular DHA, are essential to the structure and to the function of the retina (SanGiovanni, J. P. & Chew, E. Y., The role of omega-3 long-chain polyunsaturated fatty acids in health and disease of the retina, *Prog. Retin. Eye Res.,* 24, 87-138 (2005)). The highest content of omega-3 polyunsaturated fatty acids is found in the outer membranes of the retinal photoreceptor cells (Fliesler, S. J. & Anderson, R. E., Chemistry and metabolism of lipids in the vertebrate retina, *Prog. Lipid Res.* 22, 79-131 (1983)), where they carry out significant biological functions by means of anti-inflammatory, anti-apoptotic and anti-angiogenic activities. In post-mortem studies, the concentration of DHA was significantly lower in the eyes suffering from a retinal pathology than in the controls of the same age (Liu, A., Chang, J., Lin, Y., Shen, Z. & Bernstein, P. S. Long-chain and very long-chain polyunsaturated fatty acids in ocular aging and age-related macular degeneration, *J. Lipid Res.,* 51, 3217-3229 (2010)).

According to an embodiment, the retinal pathology linked to a deficit of omega-3 polyunsaturated fatty acids is a retinopathy such as age-related macular degeneration, diabetic retinopathy, retinopathy of prematurity.

Ocular neovascularization is the most common cause of blindness, this being in all populations of patients, irrespective of their age: retinopathy of prematurity in infants, diabetic retinopathy in adults and age-related macular degeneration in elderly people. An animal model was developed in order to study retinopathy (evaluation of the appearance of retinal new blood vessels, and of the growth of these vessels after lesion on a mouse eye).

The influence of omega-3 and omega-6 polyunsaturated fatty acids on vascular growth after lesion and the pathological neovascularization thus induced were studied on a mouse model having a hypoxia-induced retinopathy. It was demonstrated that the increase in intakes of omega-3 polyunsaturated fatty acids reduces pathological angiogenesis.

Taking an omega-3 polyunsaturated fatty acid supplement would therefore be advantageous in the prevention of retinopathy (Kip M Connor et al., (2007), Increased dietary intake of ω-3-polyunsaturated fatty acids reduces pathological retinal angiogenesis, Nature Medicine; doi:10.1038/nm1591).

Age-Related Macular Degeneration (AMD)

According to one embodiment, the pathology is age-related macular degeneration (AMD).

It has in fact been demonstrated that the content of polyunsaturated fatty acids in the retina of subjects suffering from AMD was reduced (Liu, A., Chang, J., Lin, Y., Shen, Z. & Bernstein, P. S., Long-chain and very long chain polyunsaturated fatty acids in ocular aging and age-related macular degeneration, J. Lipid Res., 51, 3217-3229 (2010)).

Many publications have also described the reduction in the risk of AMD associated with a high dietary intake of omega-3 polyunsaturated fatty acids (Chong, E. W., Kreis, A. J., Wong, T. Y., Simpson, J. A. & Guymer, R. H., Dietary omega-3 fatty acid and fish intake in the primary prevention of age-related macular degeneration: a systematic review and meta-analysis, Arch. Ophthalmol., 126, 826-833 (2008)), and also the reduction in the risk of AMD associated with a high blood concentration of omega-3 polyunsaturated fatty acids (Merle B M, DElyfer M N, Korobelnik J F, Rougier M B, Malet F, Feart C, Le Goff M, Peuchant E, Letenneur L, Dartigues J F, Colin J, Barberger-Gateau P, Delcourt C., High Concentrations of Plasma n3 Fatty Acids Are Associated with Decreased Risk for Late Age-Related Macular Degeneration, J. Nutr. 143: 505-11 (2013)).

The early and intermediate stages of AMD comprise deterioration in the pigment epithelium of hypo- and/or hyperpigmentation type and drusen and are not responsible for significant change in visual function.

The late stages (AMD) correspondent to the exudative (wet or neovascular) forms and to the atrophic (dry) forms, responsible for severe deterioration of the central vision. According to the studies, the prevalence of exudative AMD represents 35% to 65% of the late stages.

Early and Intermediate AMD:

Early and intermediate AMD combine one or more of the following elements together:

intermediate drusen: small asymptomatic yellowish spots observed in the perimacular region (diameter between 63 μm and 125 μm);

large drusen (also referred to as "serous" drusen): drusen of larger size (greater than 125 μm), usually asymptomatic but which may be accompanied by a reduction in night vision;

pigment deteriorations of the type of hypopigmentation or hyperpigmentation of the pigment epithelium. They reflect the death of cells of the pigment epithelium.

Exudative AMD

Exudative AMD is characterized by the proliferation of choroidal neovessels which pass through Bruch's membrane and grow under the pigment epithelium or in the subretinal space.

Atrophic AMD

Atrophic AMD (or geographic atrophy) is characterized by one or more ranges of depigmentation of the retina, of at least 175 μm in diameter, with sharp edges and an increased visibility of the choroidal vessels.

The simplified classification in four stages for the diagnosis and monitoring of AMD may be used, as represented in Table 3 (Ferris F L 3rd, Wilkinson C P, Bird A, Chakravarthy U, Chew E, Csaky K, Sadda S R, Clinical classification of age-related macular degeneration, Ophthalmology, 2013; 120: 844-51).

TABLE 3

| Category 1: no AMD (no abnormalities or abnormalities due to aging) | No drusen or a few small drusen (diameter of less than 63 µm); no pigmentary abnormalities (hypo-and hyper-pigmentation) |
| --- | --- |
| Category 2: early AMD | Intermediate drusen (between 63 and 125 µm), in the absence of large drusen (greater than 125 µm) Absence of pigmentary abnormalities |
| Category 3: intermediate AMD | Large drusen (greater than 125 µm) and/or pigmentary abnormalities |
| Category 4: late AMD | Neovascular or atrophic AMD |

The late forms of AMD correspond to category 4 and include the neovascular forms and geographic atrophy. These are patients who generally already have a decline in visual acuity.

Diabetic Retinopathy

Diabetic retinopathy (DR) is a microvascular complication of diabetes representing the primary cause of blindness in the United States and in Europe before the age of 50.

The excess sugar in the blood weakens the wall of the capillaries. This is followed by the rupture then bursting of the retinal vessels. Gradually, extended areas of the retina are no longer oxygenated. In response, the retina produces new, even weaker vessels. The phenomenon escalates and extends to the macula where the center of vision is located. The macula thickens, macular oedema occurs, which is then responsible for a decline in visual acuity which may be very significant and only partially reversible (Federation Francaise des Diabétiques la rétinopathie diabétique et les maladies des yeux [French Federation of Diabetics, diabetic retinopathy and eye diseases]).

Long-chain polyunsaturated fatty acids (LCPUFA), such as docosahexaenoic acid (DHA, C:22 6n-3) and arachidonic acid (AA, C20:4n-6) play a key role in the pathogenesis of diabetes, in the same way as the metabolisms of glucose and of lipids.

It has been demonstrated that LCPUFAs of the n-3 family inhibit many cellular and biochemical processes involved in the physiopathology of diabetic retinopathy and prevent retinal vascular damage caused by diabetes (Koehrer P, Saab S, Berdeaux O, Isaico R, Gregoire S, et al., (2014) Erythrocyte Phospholipid and Polyunsaturated Fatty Acid Composition in Diabetic Retinopathy, PLoS ONE 9(9): e106912. doi:10.1371/journal.pone.0106912).

Sala-Vila, A. et al. (Dietary Marine ω-3 Fatty Acids and Incident Sight-Threatening Retinopathy in Middle-Aged and Older Individuals With Type 2 Diabetes: Prospective Investigation From the PREDIMED Trial, JAMA Ophthalmol., 134 (10): 1142-1149 (2016)), and also Sasaki, M. et al. (The Associations of Dietary Intake of Polyunsaturated Fatty Acids With Diabetic Retinopathy in Well-Controlled Diabetes, Invest. Ophthalmol. Vis. Sci., 56 (12): 7473-7479 (2015)) also demonstrated abnormalities in the metabolism of omega-3 polyunsaturated fatty acids in subjects suffering from diabetic retinopathy.

Many articles also show a prevention of retinal disorders resulting from diabetes in animals (Shen, J. H. et al., Effect of α-linolenic acid on streptozotocin-induced diabetic retinopathy indices in vivo, Arch. Med. Res., 44 (7), 514-520 (2013), Tikhonenko, M. et al., N-3 Polyunsaturated Fatty Acids Prevent Diabetic Retinopathy by Inhibition of Retinal Vascular Damage and Enhanced Endothelial Progenitor Cell Reparative Function, PLoS One 8 (1): e55177 (2013), Sapieha, P. et al., Omega-3 polyunsaturated fatty acids preserve retinal function in type 2 diabetic mice, Nutr. Diabetes 23; 2: e36. doi: 10.1038/nutd.2012.10 (2012), Tikhonenko, M. et al., Remodeling of Retinal Fatty Acids in an Animal Model of Diabetes: A Decrease in Long-Chain Polyunsaturated Fatty Acids Is Associated With a Decrease in Fatty Acid Elongases Elovl2 and Elovl4, Diabetes, 59 (1): 219-227 (2010)).

Retinopathy of Prematurity

Retinopathy of prematurity (ROP) is a neurovascular disease affecting premature infants. This pathology is induced by a variety of factors which induce a first phase of reducing the growth of retinal vessels and of microvascular degeneration and a second phase of pathological neovascularisation, which may result in detachment of the retina.

The development of the brain and of the retina takes place during the third trimester of pregnancy. Long-chain polyunsaturated fatty acids are selectively transferred from the mother to the fetus. Among these, docosahexaenoic acid (DHA) and arachidonic acid (AA) are the most abundant.

With standard treatments, premature infants receive insufficient amounts of DHA and AA as is attested to by the low serum content of these fatty acids.

The results of in vivo studies on animals, comparing the nutritional intakes of omega-3 and omega-6, suggest that these essential dietary lipids affect retinal health. Research carried out on long-chain polyunsaturated fatty acids is mainly focused on the role of omega-3 and has demonstrated that long-chain polyunsaturated fatty acids and more particularly DHA is essential for brain and eye development.

It has also been observed that the low arachidonic acid serum levels might be involved in the pathogenesis of retinopathy of prematurity (Chatarina A. Lofqvist, PhD; Svetlana Najm, MD; Gunnel Hellgren, PhD; Eva Engström, MD, PhD; Karin Sävman, MD, PhD; Anders K. Nilsson, PhD; Mats X. Andersson, PhD; Anna-Lena Hård, MD, PhD; Lois E. H. Smith, MD, PhD; Ann Hellström, MD, PhD, 2018, Association of Retinopathy of Prematurity With Low Levels of Arachidonic Acid, A Secondary Analysis of a Randomized Clinical Trial, JAMA Ophthalmol. doi: 10.1001/jamaophthalmo1.2017.6658).

This demonstration of the abnormalities in the metabolism of omega-3 polyunsaturated fatty acids in infants suffering from retinopathy of prematurity has also been described by Pallot, C. et al. (Alteration of erythrocyte membrane polyunsaturated fatty acids in preterm newborns with retinopathy of prematurity, Sci. Rep. 9, 7930 (2019)) and Martin, C. R. et al. (Decreased postnatal docosahexaenoic and arachidonic acid blood levels in premature infants are associated with neonatal morbidities, J. Pediatr. 159, 743-749, e741-742 (2011)).

Two articles also show the effects of omega-3 polyunsaturated fatty acids and the oxygenated derivatives thereof on the retinal phenotype in an animal model of retinopathy of prematurity (Connor, K. M. et al., Increased dietary intake of omega-3-polyunsaturated fatty acids reduces pathological retinal angiogenesis, Nat. Med. 13, 868-873 (2007) and Stahl, A. et al., Lipid metabolites in the pathogenesis and treatment of neovascular eye disease, Br. J. Ophthalmol. 95, 1496-1501 (2011)).

Prevention Method

The terms "prevention" or "prevention method" are not absolute terms and, when they applied to a retinal pathology associated with a deficit of omega-3 polyunsaturated fatty acids such as a retinopathy, they denote a procedure or plan of action designed, even with a low probability of success, but that must induce an overall beneficial effect such as delay of the appearance of the pathology, or reduction of the gravity of one or more symptoms or the stabilization of the pathology.

Typically, in the case of AMD and diabetic retinopathy, prevention includes the prevention of the pathology but also the prevention of the worsening of the pathology.

The prevention of AMD or of diabetic retinopathy includes the delay in the appearance of the pathology.

The prevention of the worsening of AMD or of diabetic retinopathy includes the delay in the loss of vision or in the loss of visual acuity in the patient suffering from AMD or diabetic retinopathy.

Typically, in the case of retinopathy of prematurity, the prevention ranges from the prevention of the appearance of the pathology to the prevention of the severity of the pathology.

Typically, an increase in the content of omega-3 polyunsaturated fatty acids in the retina is associated with a reduction in the risk of appearance and/or worsening of the pathology and/or severity.

The prevention method according to the invention is an in vitro prevention method based on the in vitro determination of the content of omega-3 polyunsaturated fatty acids in the retina. The determination is in fact carried out on a blood sample chosen from whole blood, serum and plasma, preferentially plasma.

Method for Treating a Retinal Pathology Linked to a Deficit of Omega-3

The invention also relates to a method for treating a retinal pathology linked to a deficit of omega-3 polyunsaturated fatty acids comprising:

the determination of the content of omega-3 polyunsaturated fatty acids in the retina of a subject comprising the quantification of the content of at least 1 cholesteryl ester in a blood sample from said subject, the content of omega-3 polyunsaturated fatty acids in the retina being correlated to the content of said at least one cholesteryl ester, said at least one cholesteryl ester being cholesteryl 5,8,11,14,17-eicosapentaenoate;

the administration of a treatment to the subject who is in need thereof.

Typically, the retinal pathology linked to a deficit of omega-3 polyunsaturated fatty acids is a retinopathy such as age-related macular degeneration, diabetic retinopathy and retinopathy of prematurity.

Thus, the invention also relates to a method for treating age-related macular degeneration comprising:

the determination of the content of omega-3 polyunsaturated fatty acids in the retina of a subject comprising the quantification of the content of at least 1 cholesteryl ester in a blood sample from said subject, the content of omega-3 polyunsaturated fatty acids in the retina being correlated to the content of said at least one cholesteryl ester, said at least one cholesteryl ester being cholesteryl 5,8,11,14,17-eicosapentaenoate;

the administration of a treatment to the subject who is in need thereof.

Typically, said treatment will be able to be chosen from a nutritional supplement based on omega-3 polyunsaturated fatty acids optionally combined with the administration of vitamins and minerals.

The invention also relates to a method for treating diabetic retinopathy comprising:

the determination of the content of omega-3 polyunsaturated fatty acids in the retina of a subject comprising the quantification of the content of at least 1 cholesteryl ester in a blood sample from said subject, the content of omega-3 polyunsaturated fatty acids in the retina being correlated to the content of said at least one cholesteryl ester, said at least one cholesteryl ester being cholesteryl 5,8,11,14,17-eicosapentaenoate;

the administration of a treatment to the subject who is in need thereof.

Typically, said treatment will be able to be chosen from a nutritional supplement based on omega-3 polyunsaturated fatty acids optionally combined with the administration of vitamins and minerals.

The invention also relates to a method for treating retinopathy of prematurity comprising:

the determination of the content of omega-3 polyunsaturated fatty acids in the retina of a subject comprising the quantification of the content of at least 1 cholesteryl ester in a blood sample from said subject, the content of omega-3 polyunsaturated fatty acids in the retina being correlated to the content of said at least one cholesteryl ester, said at least one cholesteryl ester being cholesteryl 5,8,11,14,17-eicosapentaenoate;

the administration of a treatment to the subject who is in need thereof.

Typically, said treatment will be able to be chosen from a nutritional supplement based on omega-3 polyunsaturated fatty acids optionally combined with the administration of vitamins and minerals.

Method for Monitoring the Treatment of a Retinal Pathology Linked to a Deficit of Omega-3 Polyunsaturated Fatty Acids The invention relates to a method for monitoring the treatment of a pathology linked to a deficit of omega-3 polyunsaturated fatty acids comprising the steps:

of administering at least one treatment;

of determining the content of omega-3 polyunsaturated fatty acids in the retina according to the determination method according to the invention.

The invention also relates to a method for monitoring the treatment of a pathology linked to a deficit of omega-3 polyunsaturated fatty acids comprising the determination of the content of omega-3 polyunsaturated fatty acids in the retina of a patient to whom a treatment has been administered, according to the determination method according to the invention.

Typically, the treatment is a nutritional supplement based on omega-3 polyunsaturated fatty acids optionally combined with the administration of vitamins and minerals.

According to an embodiment, the pathology is a retinopathy chosen from age-related macular degeneration, diabetic retinopathy and retinopathy of prematurity.

Among the emerging preventative strategies, omega-3 polyunsaturated fatty acids make it possible to promote normal retinal structure and function and also to reduce the incidence and slow down the progression of AMD (SanGiovanni, J. P. & Chew, E. Y., The role of omega-3 long-chain polyunsaturated fatty acids in health and disease of the retina, Prog. Retin. Eye Res., 24, 87-138 (2005)) but also to prevent all retinopathies (Kip M Connor et al., (2007), Increased dietary intake of ω-3-polyunsaturated fatty acids reduces pathological retinal angiogenesis, Nature Medicine; doi:10.1038/nm1591).

Typically, an increase in the content of omega-3 polyunsaturated fatty acids of the content of the retina is synonymous with efficacy of the treatment.

The monitoring method according to the invention is an in vitro monitoring method based on the in vitro determination of the content of omega-3 polyunsaturated fatty acids in the retina. The determination is in fact carried out on a blood sample chosen from whole blood, serum and plasma, preferentially plasma.

Method for Diagnosis of Deficiencies in Omega-3 Polyunsaturated Fatty Acids

The invention relates to a method for diagnosis of deficiencies in omega-3 polyunsaturated fatty acids comprising the determination of the content of omega-3 polyunsaturated fatty acids in the retina according to the determination method according to the invention.

The expression "deficiencies in omega-3 polyunsaturated fatty acids" is understood to mean a deficit of polyunsaturated fatty acids relative to a healthy subject, i.e. a subject who does not have deficiencies in polyunsaturated fatty acids.

Typically, a reduction in the content of omega-3 polyunsaturated fatty acids of the content of the retina is synonymous with deficiency in omega-3 polyunsaturated fatty acids.

In one embodiment, the comparison with a control sample is carried out. The expression "control sample" is understood to mean the distribution of the values in healthy subjects, i.e. subjects who do not have deficiencies in polyunsaturated fatty acids. The content of omega-3 polyunsaturated fatty acids in the retina of the healthy subjects of the control group is determined by the method according to the invention.

The diagnosis method according to the invention is an in vitro diagnosis method based on the in vitro determination of the content of omega-3 polyunsaturated fatty acids in the retina. The determination is in fact carried out on a blood sample chosen from whole blood, serum and plasma, preferentially plasma.

EXAMPLES

In the examples that follow, the inventors have determined the circulating lipids that have the highest predictive performance in order to determine the content of omega-3 polyunsaturated fatty acids in the retina.

In these examples, data originating from collection of eyes and blood from donors has made it possible to establish an algorithm based on the plasma concentration of seven species of cholesteryl esters, making it possible to determine the retinal content of omega-3 fatty acids (example 1).

The inventors have furthermore demonstrated the association between AMD and retinal status of omega-3 polyunsaturated fatty acids (example 2) and also the impact of a dietary supplement of omega-3 polyunsaturated fatty acids (example 3), thus showing that the combination of these seven cholesteryl esters constitutes a biomarker that makes it possible to develop a personalized medicine in order to identify subjects at risk of retinopathy and more particularly AMD and/or to monitor supplements of omega-3 polyunsaturated fatty acids. The predictive capacity of cholesteryl 5,8,11,14,17-eicosapentaenoate alone has also been demonstrated in example 4.

Materials and Methods

In the examples that follow, the materials and methods given in detail below were used.

The studies on human subjects were carried out in accordance with the directives of the Declaration of Helsinki. Written consents were obtained and the protocols were accepted by the local ethics committees (CPP Sud Est I, university hospital, Saint Etienne, France; CPP Est III, university hospital, Dijon, France; CPP Sud-Ouest et Outre Mer III, university hospital, Bordeaux, France).

Donor Study

Human eyeballs, plasma and erythrocytes were obtained from 46 donors (bodies donated to science, 30 women and 16 men, median age 86.5 years, interquartile range 76-92 years). The tissues were collected and prepared according to the procedures already described and known to a person skilled in the art. The samples were stored at −80° C. until other analyses.

Case-Control Study

The subjects were selected from 2 studies in progress in Bordeaux (Alienor study) and in Dijon (Montrachet study), which used similar methods. Between 2009 and 2011, the participants were aged 75 years or more and had undergone an eye examination and a fasting blood collection. The eye examinations took place in the ophthalmology departments of the university hospitals of Bordeaux and Dijon, and consisted of an ophthalmological history, measurements of visual acuity and of refraction and two 45° non-mydriatic retinographs. The retinal photographs were interpreted in accordance with the international classification and with a modification of the classification system used in the Multi-Ethnic Study of Atherosclerosis for the size, location and surface area of the drusen. The participants were classified according to their worst eye into the following three exclusive groups:

no AMD, early AMD (presence of serous drusen (>125 microns) and/or reticular drusen and/or pigmentary abnormalities);

late AMD (geographic atrophy or neovascular disease).

The cases of AMD were suffering from late AMD (geographic atrophy or neovascular disease) and the controls were free of any form of early or late AMD and had a visual acuity of greater than 20/40. The exclusion criteria for both cases and the controls were the presence of glaucoma and the presence of diabetes. 31 cases were identified from the participants having undergone an eye examination and a fasting blood collection between 2009 and 2011 and the controls were matched in a 1:1 ratio for age (+/−2 years), sex and use of hypolipidemic drugs. The plasma samples were stored at −80° C. until analysis of the lipids.

Supplementation Study

Plasma samples were obtained from 55 subjects participating in the double-blind, randomized clinical trial entitled "Lutein Influence on Macula of Persons Issued From AMD Parents (LIMPIA)" (Korobelnik J F, Rougier M B, Delyfer M N, Bron A, Merle B M J, Savel H, Chene G, Delcourt C, Creuzot-Garcher C., Effect of Dietary Supplementation With Lutein, Zeaxanthin, and Omega-3 on Macular Pigment: A Randomized Clinical Trial, JAMA Ophthalmol., 2017; 135: 1259-66). Adult participants in good health aged from 40 to 70 years were recruited. Each participant was randomized in a 1:1 ratio to receive either two capsules per day of a dietary supplement containing lutein, zeaxanthin, vitamin C, vitamin E, zinc, copper, resveratrol and also fish oil rich in omega-3 polyunsaturated fatty acids (Nutrof Total, Laboratoires Théa) or a placebo containing paraffin. Blood samples were collected at the start and after 3 and 6 months of supplementation. The whole blood was centrifuged at 3000 rpm for 10 minutes at 4° C. to isolate the plasma from the red blood cells. The plasma samples were stored at −80° C. until a more advanced analysis.

Statistical Analyses

Donor study: The model with the lowest prediction error was obtained using an extension of the partial least squares regression method (sgPLS or sparse group PLS) described by Liquet et al. (Liquet B et al., Bioinformatics, 2016, Jan. 1; 32(1): 35.42).

Case-control study: The differences between the cases and the controls for the predicted content of omega-3 polyunsaturated fatty acids in the retina, the total omega-3 polyunsaturated fatty acids in the plasma and in the red blood cells were evaluated by mixed linear regression adjusted as a function of age, body mass index, smoking, the use of the omega-3 supplement, HDL cholesterol and LDL cholesterol, with a random factor for the case-control pairs.

Supplementation study: The plasma concentrations of cholesteryl esters and the predicted content of omega-3 polyunsaturated fatty acids in the retina were compared between the participants under supplementation and the participants under placebo using linear regression models adjusted as a function of age, sex, body mass index (BMA), and HDL and LDL cholesterol.

All the p values below 0.05 were considered to be statistically significant. The analyses for the case-control and supplementation studies were carried out using SAS software (SAS, version 9.4; SAS Institute Inc., Cary, North Carolina, United States).

Example 1: Identification of a Biomarker of the Content of Omega-3 Polyunsaturated Fatty Acids in the Retina Rationale Blood is a complex fluid composed of cellular elements comprising white blood cells and red blood cells, platelets, and a liquid portion referred to as plasma. Blood lipids are mainly found in the membranes of the red blood cells and in plasma lipoprotein particles. The membranes of the red blood cells are almost exclusively constituted of phospholipids. Due to a lifespan of around 120 days, the fatty acid composition of the phospholipids of the red blood cells is representative of the long-term dietary intake of the lipids. Furthermore, the plasma lipoproteins transport biologically important lipid compounds, such as chylomicrons and very-low-density lipoproteins (VLDL) which are structures that transport mainly the triglycerides formed in the intestine and in the liver respectively from dietary lipids and carbohydrates. The fatty acid compositions thereof are associated with the very short term dietary intake. In contrast, low-density lipoproteins (LDL) and high-density lipoproteins (HDL) are involved in the two-way transport of lipids between the liver and the peripheral tissues. They are enriched in phospholipids (in particular the subclass of phosphatidylcholine) and in cholesteryl esters. The fatty acid compositions of LDL and HDL are considered to be indications of the medium-term consumption of dietary fats.

In order to determine if the lipids of one or more of these blood compartments could constitute reliable indicators of the content of omega-3 polyunsaturated fatty acids in the retina and of omega-3 polyunsaturated fatty acid supplementation, the BLISAR (Biomarkers of LIpid Status And metabolism in Retinal ageing) study was carried out between 2015 and 2018.

Results

The blood and the ocular tissues of 46 human donors from the Université de Saint-Etienne [University of Sainte-Etienne] (bodies donated to science) were analysed in order to determine the fatty acid composition thereof by lipidomics. In addition to the retinal and total plasma lipids, the long-term and medium-term markers of dietary lipids were studied by isolating and analysing the fatty acid compositions of the plasma (total lipids, phosphatidylcholines and cholesteryl esters) and also of the red blood cells. The fatty acid profiles confirmed the quantitative importance of omega-3 polyunsaturated fatty acids in the retina (16.8% versus 3.4% in the red blood cells and 2.9% in the total lipids of the plasma).

Via a lipidomic analysis, a set of data on the lipids present in the 4 blood compartments (red blood cells, total plasma, plasma phosphatidylcholines and plasma cholesteryl esters), corresponding to 332 different species was generated.

The model with the lowest prediction error was obtained using an extension of the partial least squares regression method (sgPLS or sparse group PLS) and was characterized by a correlation coefficient of 0.62 between the observed and predicted values of the content of omega-3 polyunsaturated fatty acids in the retina, obtained by cross validation. This predictor of the content of omega-3 polyunsaturated fatty acids in the retina is based on an algorithm combining the plasma concentrations of 7 species of cholesteryl esters.

Three of the cholesteryl esters identified are from the family of omega-3 polyunsaturated fatty acids, i.e. cholesteryl 5,8,11,14,17-eicosapentaenoate, cholesteryl 9,12,15-octadecatrienoate and cholesteryl 4,7,10,13,16,19-docosahexaenoate.

The other four cholesteryl esters are from the family of omega-6 polyunsaturated fatty acids, namely cholesteryl 9,12-octadecadienoate, cholesteryl 6,9,12-octadecatrienoate, cholesteryl 8,11,14-eicosatrienoate and cholesteryl 5,8,11,14-eicosatetraenoate.

The methyl esters of the aforementioned cholesteryl esters are used in order to determine and measure the relative amount of the fatty acids of the cholesteryl esters. The method for determining the content of omega-3 polyunsaturated fatty acids is given in detail below:

Method for Determining the Content of Omega-3 Polyunsaturated Fatty Acids in the Retina The method for determining omega-3 polyunsaturated fatty acids in the retina is broken down into several steps:

1. blood collection and isolation of the plasma;
2. extraction of the total lipids from the plasma;
3. isolation of the cholesteryl esters from the total lipids;
4. formation of the methyl esters of the fatty acids of the cholesteryl esters, in other words methyl esters are formed from the fatty acid resulting from the hydrolysis of the cholesteryl ester;
5. determination of the relative amounts of 25 methyl esters of fatty acids of the cholesteryl esters;
6. calculation of the estimated value of the content of omega-3 polyunsaturated fatty acids in the retina from the relative amounts of fatty acid methyl esters of 7 cholesteryl esters.

Blood Collection and Isolation of the Plasma

A sample of blood is collected from a human subject by venipuncture into a tube treated with EDTA, citrate or heparin. The tube containing the whole blood is centrifuged at 3000 rpm for 10 minutes at 4° C. in order to separate the plasma from the red blood cells. The upper phase containing the plasma is drawn off and stored in a dry tube. The total lipids of the plasma can be extracted immediately or the plasma sample can be frozen while awaiting the rest of the procedures.

Extraction of the Total Lipids of the Plasma

The total lipids of the plasma are extracted by the method of Moilanen & Nikkari (Moilanen & Nikkari, Clin. Chim. Acta, 1981; 114(1): 111.116). In a glass tube, 5 milliliters of a chloroform/methanol (1:1, v:v) mixture are added to a volume of around 450 microliters of plasma. The tube is vortex mixed for 1 minute then centrifuged at 3000 rpm for 3 minutes. The upper phase is isolated in another glass tube using a Pasteur pipette. Four milliliters of chloroform are added to this second tube and also 3 milliliters of acidic sodium chloride (17 mmol/L). The tube is vortex mixed for 1 minute then centrifuged at 3000 rpm for 3 minutes. The upper phase is removed using a Pasteur pipette then the lower phase containing the extract of the plasma lipids is isolated in a glass sample vial. The extract of total lipids is firstly dried under a stream of nitrogen then diluted in chloroform to a concentration of 10 mg/ml. The cholesteryl esters can be isolated immediately from the total lipids or else frozen while awaiting the rest of the procedures.

Isolation of the Cholesteryl Esters from the Total Lipids

The cholesteryl esters are isolated from the total lipids according to a procedure described in Bretillon et al., 2008 (Bretillon et al., Exp. Eye Res., 2008; 87(6): 521-528). A glass plate covered with silica gel is prewashed in a migration tank containing 100 mL of ethyl acetate. It is then placed in an oven at 120°, for 30 minutes in order to be activated. The total lipids extracted are deposited on the plate in the form of a band of around 3 cm using a glass syringe, then the plate is placed for 25 to 30 minutes in a chromatographic migration tank containing 101 milliliters of a hexane/ethyl ether/ethyl acetate (80:20:1, v:v:v) mixture. The plate is then removed from the tank and left under a fume hood for a few minutes. It is then exposed to vaporization of 2',7'-dichlorofluorescein and then observed under ultraviolet light at 366 nm. The band of silica containing the cholesteryl esters which is located at around 8 to 9 cm from the deposit is marked using a pencil then scratched off using a razor blade in order to be recovered in a glass tube to which 1 milliliter of toluene is added. The isolated cholesteryl esters may be transmethylated immediately in preparation for chromatographic analysis or else stored at 4° C. while awaiting the rest of the procedures.

Formation of the Methyl Esters of the Fatty Acids of the Cholesteryl Esters

The methyl esters of the fatty acids of the cholesteryl esters are formed by transmethylation according to the method of Morrison & Smith (Morrison & Smith, J. Lipid Res., 1964; 53: 600.608). One milliliter of a boron trifluoride/methanol (1:1, v:v) mixture is added to the tube containing the silica gel with the cholesteryl esters and the toluene. The tube is placed in an oven at 95° C. for 2 hours. It is then cooled to ambient temperature. After adding 5 milliliters of sodium bicarbonate and 5 milliliters of hexane, the tube is vortex mixed for 1 minute then centrifuged at 3000 rpm for 3 minutes. The upper phase is isolated in a glass tube using a Pasteur pipette. After drying the methyl esters of the fatty acids of the cholesteryl esters under a stream of nitrogen, they are diluted in 1 milliliter of hexane. The methyl esters of the fatty acids of the cholesteryl esters may be analysed immediately by gas chromatography or stored at 4° C. while awaiting the rest of the procedures.

Determination of the Profile of the Fatty Acids of the Cholesteryl Esters

The profile of the fatty acids of the cholesteryl esters is determined by gas chromatography coupled to flame ionization detection according to Acar et al. (Acar et al. PLoS One 2012; 7(4): e35102). The methyl esters of the fatty acids of the cholesteryl esters are injected to a gas chromatograph equipped with a CPSIL88 column (100 m×0.25 mm in internal diameter, film thickness of 0.20 μm, Varian, Les Ulis, France). Hydrogen is used as carrier gas at a pressure of 210 kPa. The temperature of the oven of the chromatograph is 60° C. for 5 minutes, then increased to 165° C. at 15° C. per minute. After being held at 165° C. for 1 minute, it is increased to 225° C. at 2° C. per minute. It is held at 225° C. for 17 minutes. The temperatures of the injector and of the detector are set at 250° C. The fatty acid methyl esters are identified by comparison of their retention times with those of commercial standards. The relative proportions of the 25 species of methyl esters are calculated using EZChrom Elite software (Agilent Technologies, Massy, France) and expressed as a percentage of the total fatty acids of the cholesteryl esters.

Calculation of the Estimated Value of the Content of Omega-3 Polyunsaturated Fatty Acids in the Retina Use of the relative % of 7 methyl esters of fatty acids of the cholesteryl esters: 9,12,15-octadecatrienoic acid methyl ester (C18:3n-3 methyl ester), 5,8,11,14,17-eicosapentaenoic acid methyl ester (C20:5n-3 methyl ester), 4,7,10,13,16,19-docosahexaenoic acid methyl ester (C22:6n-3 methyl ester), 9,12-octadecadienoic acid methyl ester (C18:2n-6 methyl ester), 6,9,12-octadecatrienoic acid methyl ester (C18:3n-6 methyl ester), 8,11,14-eicosatrienoic acid methyl ester (C20:3n-6 methyl ester), 5,8,11,14-eicosatetraenoic acid methyl ester (C20:4n-6 methyl ester). The mathematical algorithm makes it possible to predict, for a new sample (test sample), the content of omega-3 polyunsaturated fatty acids in the retina from the assay of the 7 molecules of cholesteryl esters in the plasma which are presented above. This algorithm is based on the sparse group partial least squares {sgPLS} method described by Liquet et al. (Liquet B et al., Bioinformatics, 2016, Jan. 1; 32(1): 35.42), which was applied to samples of retina, plasma and red blood cells collected from 46 human donors (training sample).

The mathematical algorithm consists of 4 steps:
1. Several sums and ratios are calculated from the assays of the 7 molecules of interest.
2. All of the parameters are centered and reduced using the means and standard deviations of the training sample (which assumes that the test sample is derived from the same distribution as the training sample).
3. The model obtained by sgPLS is applied to the values obtained in step 2.
4. In order to obtain the prediction of the concentration of omega-3 polyunsaturated fatty acids in the retina, the result obtained in step 3 is multiplied by the standard deviation of the concentration of omega-3 polyunsaturated fatty acids in the retina of the training sample. The values thus obtained are added to the mean of the concentration of omega-3 polyunsaturated fatty acids in the retina of the training sample.

Conclusions

Advantageously, the species of cholesteryl esters from the family of omega-3 polyunsaturated fatty acids contributed positively to the estimation of the content of omega-3 polyunsaturated fatty acids in the retina whereas those from the family of omega-6 polyunsaturated fatty acids lowered this estimated content, which is comparable with the well-established competitive metabolism of omega-3 and omega-6.

The identification of a biomarker based on the plasma concentrations of 7 specific lipid species is innovative and advantageous, since the previous studies and attempts, based on the analysis of red blood cells or of total plasma lipids, did not make it possible to establish a close correlation between the circulating lipids and the content of omega-3 polyunsaturated fatty acids in the retina.

Advantageously again, it is possible to confirm the better robustness of the prediction, this being in comparison with studies and approaches that have determined the contents of omega-3 polyunsaturated fatty acids in the red blood cells and the total blood (r=0.62 versus r=0.40 for the omega-3 fatty acids of the total lipids of the plasma and r=0.14 for the omega-3 fatty acids of the red blood cells). This indicates that a more subtle approach centered on a small number of plasma cholesteryl esters is more effective than estimating the retinal content of omega-3 polyunsaturated fatty acids.

Furthermore, the identification of the cholesteryl esters as biomarkers of the content of omega-3 polyunsaturated fatty acids in the retina reinforces the prior observations by the inventors, suggesting that these lipids are the preferential source of fatty acids for the retina.

Example 2: Association Between AMD and Retinal Status of Omega-3 Polyunsaturated Fatty Acids During the second phase of the study, the association between AMD and the status of omega-3 polyunsaturated fatty acids was studied.

Firstly, in a post-mortem case-control study, a lower content of omega-3 polyunsaturated fatty acids was observed in retinas affected by AMD (14.4%±1.9%) compared to those of donors in good health (16.8%±3.1%), thus confirming the previous observations. After adjustment for age, sex, time after death, the difference between the content of omega-3 polyunsaturated fatty acids in retinas affected by AMD and the content of omega-3 polyunsaturated fatty acids in control retinas was −2.41% (p=0.04).

Next, using the method previously described (measurement of the 25 cholesteryl esters of the plasma, application of the algorithm to these measurements), the predicted content of omega-3 polyunsaturated fatty acids in the retina was compared between 31 subjects suffering from late AMD and 31 controls matched for age, sex, and use of hypolipidemic drugs.

This predicted content of omega-3 polyunsaturated fatty acids in the retina was lower in the cases than in the controls (17.8% versus 18.9%). After adjustment as a function of age, body mass index, smoking, use of omega-3 supplement, HDL cholesterol and LDL cholesterol, the difference between the predicted content of omega-3 polyunsaturated fatty acids in the retina between the cases of AMD and the controls was −1.39% (p=0.04).

In contrast, in the red blood cells, the content of omega-3 polyunsaturated fatty acids was similar in the cases and in the controls (6.0% versus 5.6%, p=0.42, after multivariate adjustment). These observations agree perfectly with the physiopathology of AMD, characterized by the loss of the metabolism rich in omega-3 polyunsaturated fatty acids of the photoreceptor cells.

Given the crucial roles played by DHA in the retinal structure and function and the depletion thereof in the eyes of patients suffering from AMD, it is logical to maintain high retinal levels of omega-3 polyunsaturated fatty acids in order to prevent the development and/or progression of the disease.

This hypothesis was consolidated by more than 20 epidemiological studies showing a significantly reduced risk of developing AMD in subjects consuming a lot of omega-3 polyunsaturated fatty acids. However, in the two randomized trials (AREDS2 (Lutein+zeaxanthin and omega-3 fatty acids for age-related macular degeneration: the Age-Related Eye Disease Study 2 (AREDS2) randomized clinical trial, JAMA 2013; 309: 2005-15 and NAT2 Souied E H, Delcourt C, Querques G, Bassols A, Merle B, Zourdani A, Smith T, Benlian P., Oral Docosahexaenoic Acid in the Prevention of Exudative Age-Related Macular Degeneration: The Nutritional AMD Treatment 2 Study, Ophthalmology, 2013; 120: 1619-31.), supplementation with omega-3 polyunsaturated fatty acids did not modify the progression of the disease in the late stages of the disease. One possible explanation for this contradictory data probably lies in the sensitivity of the subjects to nutritional supplementation. Specifically, whilst supplementation with omega-3 polyunsaturated fatty acids had no effect on the progression of AMD when the whole of the population was taken into account, it was shown in the NAT2 study that the subjects who maintained high and constant blood levels of omega-3 polyunsaturated fatty acids had a significantly lower risk of developing late AMD. This discovery highlights the need to monitor the metabolic status of the subjects participating in nutritional interventions.

Example 3: Sensitivity to Dietary Supplementation with Omega-3 Polyunsaturated Fatty Acids of the Predicted Content of Omega-3 Polyunsaturated Fatty Acids in the Retina The sensitivity to dietary supplementation with omega-3 polyunsaturated fatty acids of the predicted content of omega-3 polyunsaturated fatty acids in the retina was therefore evaluated.

For this purpose, blood samples collected in the context of the LIMPIA randomized clinical trial in which middle-aged participants in good health received a daily dose of 676 mg of omega-3 polyunsaturated fatty acids for 6 months, or a placebo, were analysed. The interquartile range of the predicted content of omega-3 polyunsaturated fatty acids in the retina at the start varied from 17.2% to 19.7% of the total fatty acids, with median values of around 18.5% for the two groups, which is in accordance with the previous observations in middle-aged healthy subjects.

After 3 months of supplementation, the predicted content of omega-3 polyunsaturated fatty acids in the retina was significantly increased in the supplemented subjects (median values of 18.8% and 21.6% of the total fatty acids of the placebo groups and of the supplemented groups, respectively; p<0.001).

After 6 months of supplementation, this difference was maintained since the predicted content of omega-3 polyunsaturated fatty acids in the retina corresponded perfectly to that calculated at 3 months (median values of 18.9% and 21.7% of the total fatty acids of the placebo and supplemented groups, respectively; p<0.001).

Thus, and advantageously, a blood biomarker of the status of omega-3 polyunsaturated fatty acids in the retina, based on the measurement of 7 plasma lipid species, inversely correlated to the risk of late AMD and increased with supplementation with omega-3 polyunsaturated fatty acids, was identified.

This blood biomarker is thus a reliable and accurate tool for preparing and carrying out clinical trials but also makes it possible to prevent the appearance of retinal pathologies linked to a deficit of omega-3 polyunsaturated fatty acids and also to diagnose deficiencies in omega-3 polyunsaturated fatty acids.

Example 4: Calculation of the Predictive Capacity of Cholesteryl 5,8,11,14,17-Eicosapentaenoate (C20:5 ω3 Methyl Ester)

The inventors verified whether it was possible to determine the content of omega-3 polyunsaturated fatty acids in the retina from a single cholesteryl ester, cholesteryl 5,8,11, 14,17-eicosapentaenoate (C20:5 ω3 methyl ester) rather than from the 7 cholesteryl esters identified by the sgPLS method.

The result of the linear regression of the concentration of omega-3 polyunsaturated fatty acids in the retina on cholesteryl 5,8,11,14,17-eicosapentaenoate is given in detail in Table 4:

TABLE 4

|  | Coefficient | p-value |
|---|---|---|
| C20:5ω3 methyl ester | 4.1717 | 4.98e−06 |

The predictive capacity of cholesteryl 5,8,11,14,17-eicosapentaenoate was evaluated by calculating the correlation coefficient between the contents of omega-3 polyunsaturated fatty acids in the retina predicted and those observed, estimated by cross validation in the training sample of 46 donors. A correlation coefficient r equal to 0.59 is obtained.

This result shows that the predictive capacity is virtually similar to that obtained by the mathematical formula resulting from the sgPLS method (r=0.62) with only cholesteryl 5,8,11,14,17-eicosapentaenoate.

Advantageously again, it is demonstrated here that cholesteryl 5,8,11,14,17-eicosapentaenoate is a blood biomarker of the status of omega-3 polyunsaturated fatty acids in the retina, in the same way as the 7 cholesteryl esters identified.

The invention claimed is:

1. A method for determining the content of omega-3 polyunsaturated fatty acids in the retina of a subject comprising
   determining the content of at least one cholesteryl ester in a blood sample from said subject, the content of omega-3 polyunsaturated fatty acids in the retina being correlated to the content of said at least one cholesteryl ester, said at least one cholesteryl ester being cholesteryl 5,8,11,14,17-eicosapentaenoate.

2. The method as claimed in claim 1, wherein the blood sample is chosen from whole blood, serum and plasma.

3. The method as claimed in claim 1, wherein the determining step includes
   isolating plasma from the blood sample;
   extracting total lipids from the plasma;
   isolating the at least one cholesteryl ester from the total lipids;
   forming methyl esters of fatty acids resulting from hydrolysis of the at least one cholesteryl ester;
   determining a relative amount of the methyl esters; and
   calculating an estimated value of the content of omega-3 polyunsaturated fatty acids in the retina from the relative amount of fatty acid methyl esters of the at least one cholesteryl ester.

4. The method as claimed in claim 1, wherein the content of seven cholesteryl esters is determined.

5. The method as claimed in claim 4, wherein the seven cholesteryl esters are cholesteryl 5,8,11,14,17-eicosapentaenoate, cholesteryl 9,12,15-octadecatrienoate, cholesteryl 4,7,10,13,16,19-docosahexaenoate, cholesteryl 9,12-octadecadienoate, cholesteryl 6,9,12-octadecatrienoate, cholesteryl 8,11,14-eicosatrienoate, cholesteryl 5,8,11,14-eicosatetraenoate.

* * * * *